US00PP31104P2

(12) United States Plant Patent
Uria

(10) Patent No.: US PP31,104 P2
(45) Date of Patent: Nov. 19, 2019

(54) ***SALVIA* PLANT NAMED 'AMANTE'**

(50) Latin Name: ***Salvia* hybrid**
Varietal Denomination: Amante

(71) Applicant: New World Plants Limited, Herefordshire (GB)

(72) Inventor: Rolando Anibal Uria, Mar del Plata (AR)

(73) Assignee: NEW WORLD PLANTS LIMITED, Luston (GB)

( * ) Notice: Subject to any disclaimer, the term of this patent is extended or adjusted under 35 U.S.C. 154(b) by 0 days.

(21) Appl. No.: 15/932,982

(22) Filed: Jun. 1, 2018

(51) Int. Cl.
*A01H 5/02* (2018.01)
*A01H 6/00* (2018.01)

(52) U.S. Cl.
USPC ..... Plt./475
CPC ..... *A01H 6/00* (2018.05)

(58) Field of Classification Search
USPC ..... Plt./475
CPC ..... A01H 5/02
See application file for complete search history.

(56) References Cited

PUBLICATIONS https://issuu.com/yaaraender/docs/jaldety_2018; Apr. 1, 2018; 3 pages.*

* cited by examiner

*Primary Examiner* — Kent L Bell
(74) *Attorney, Agent, or Firm* — Penny J. Aguirre

(57) ABSTRACT

A new cultivar of hybrid *Salvia*, 'Amante', that is characterized by its flowers that are typical of *Salvia guaranitica* in flower type and red and pink in color with dark calyces, its long blooming habit with new shoots producing flowers throughout the summer, its early commencement of bloom, its plant height of up to 1.2 meter, and its growth habit that lacks spreading roots.

2 Drawing Sheets

Botanical classification: *Salvia* hybrid.
Variety denomination: 'Amante'.

BACKGROUND OF THE INVENTION

The present invention relates to a new and distinct cultivar of *Salvia* of hybrid origin and will be referred to hereafter by its cultivar name, 'Amante'. 'Amante' is an herbaceous perennial grown for landscape use.

The new *Salvia* arose from a breeding program conducted by the Inventor at a nursery in Mar del Plata, Argentina. The objective of the breeding program was to develop a new *Salvia* cultivar with red *Salvia guaranitic* type flowers combined with characteristics of both parents.

The new *Salvia* originated from a cross-pollination made by the Inventor in February of 2015 between *Salvia* x *westerae* 'Petra' (not patented) as the female parent and *Salvia guaranitica* 'Black & Blue' (not patented) as the male parent. 'Amante' was selected as a unique single plant from the progeny resulting from the cross-pollination in February of 2017.

Asexual propagation of the new cultivar was first accomplished by the inventor by stem cuttings in March of 2017 in Mar del Plata, Argentina. Asexual propagation by stem cutting has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Amante' as a unique cultivar of *Salvia*.

1. 'Amante' exhibits flowers that are typical of *Salvia guaranitica* in flower type that are red and pink in color with dark calyces.
2. 'Amante' commences bloom early in the season.
3. 'Amante' exhibits a long blooming habit with new shoots producing flowers throughout the summer.
4. 'Amante' exhibits a plant height of up to 1.2 meter.
5. 'Amante' exhibits growth habit that lacks spreading roots.

The female parent, 'Petra', differs from 'Amante' in having flowers that are lacking dark colored calyces, leaves that are less shiny and less broad, a shorter blooming period and a less floriferous blooming habit. The male parent, 'Black & Blue', differs from 'Amante' in having flowers that are purple in color and in having a spreading rooting habit. 'Amante' can also be most compared to the cultivars *Salvia* 'Amistad' (U.S. Plant Pat. No. 23,578) and *Salvia guaranitica* 'Black and Bloom' (U.S. Plant Pat. No. 27,183). 'Amistad' and 'Black & Blue' are both similar to 'Amante' in flower type. 'Amistad' differs from 'Amante' in having flowers that are purple in color, shorter inflorescences that are more congested, and a leaf texture that is less rugose. 'Black & Bloom' differs from 'Amante' in having flowers that are purple in color, shorter inflorescences that are more congested, leaves that are darker in color and a shorter plant height.

BRIEF DESCRIPTION OF THE DRAWINGS

The accompanying colored photographs illustrate the overall appearance and distinct characteristics of a 7-month-old plant of the new *Salvia* as grown in a two-gallon container in Loxely, Ala.

The photograph in FIG. 1 provides a side view of 'Amante'.

Figure 1:
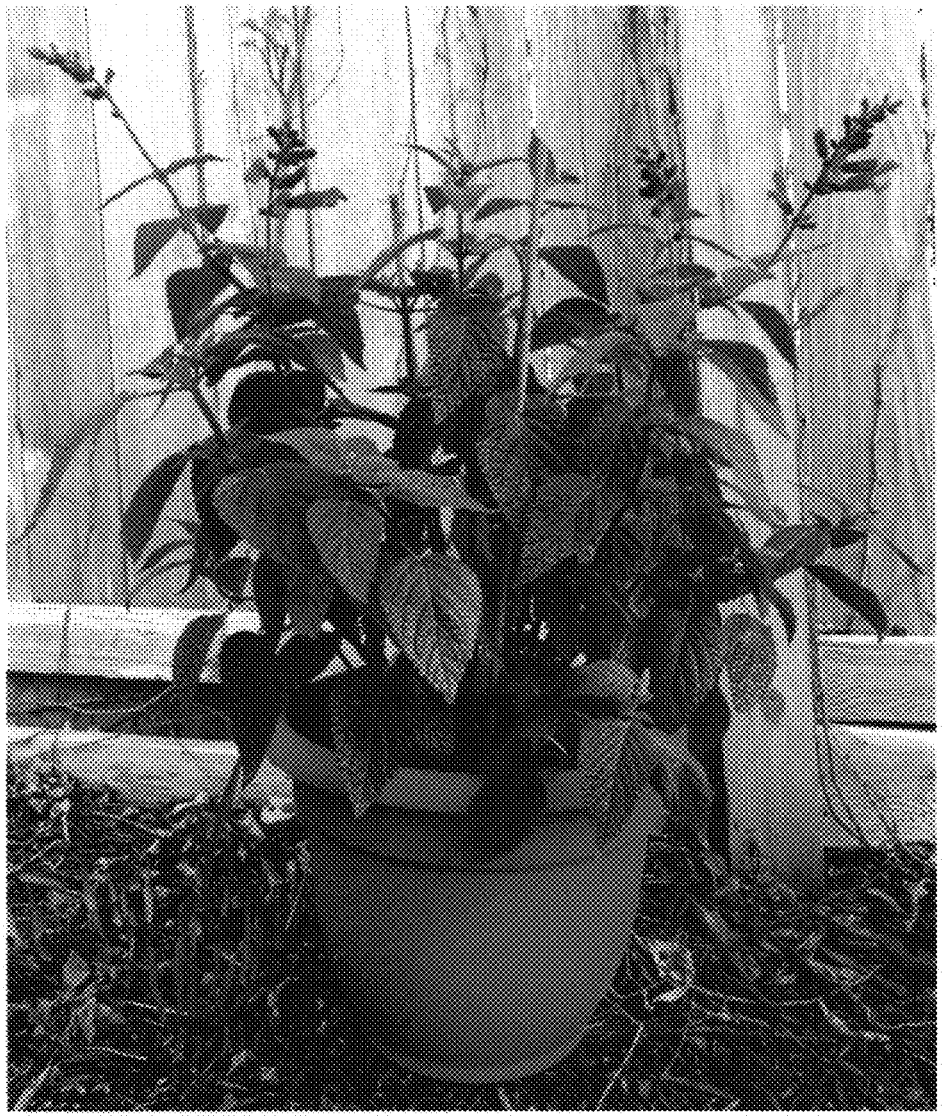
Figure 2:
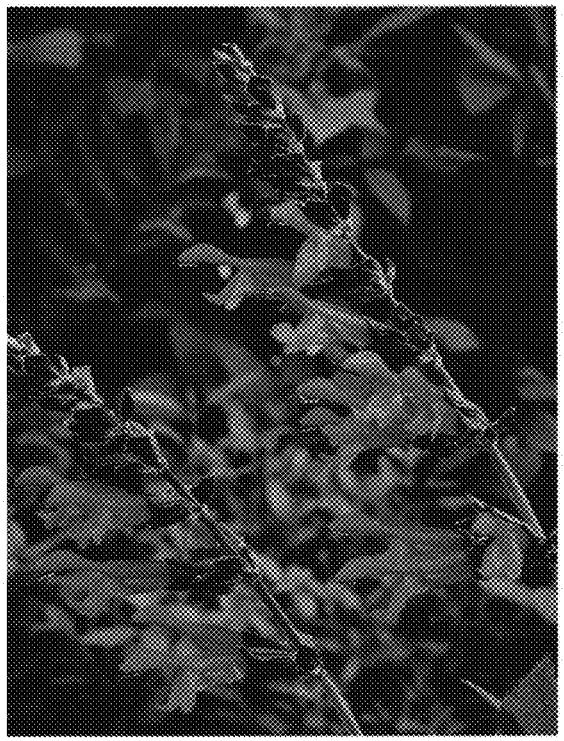

The photograph in FIG. 2 provides a close-up view of an inflorescence of 'Amante'.

Figure 3:
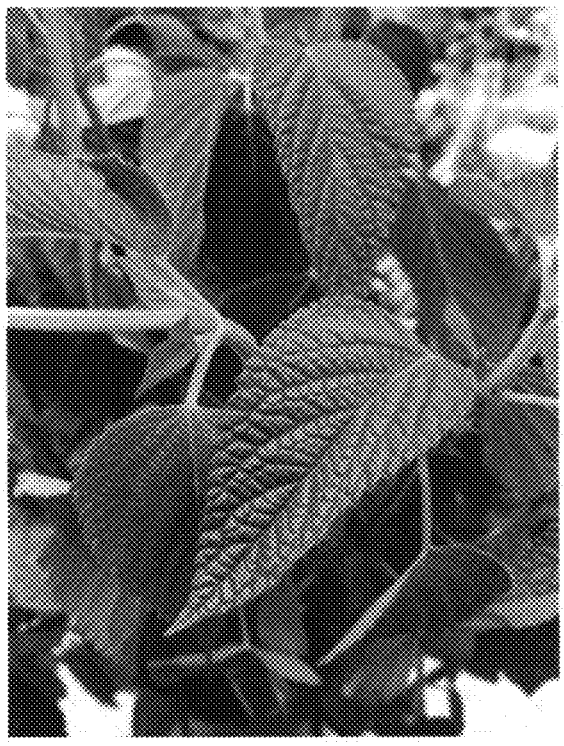

The photograph in FIG. 3 provides a close-up view of the foliage of 'Amante'.

The colors in the photographs may differ slightly from the color values cited in the detailed botanical description, which accurately describe the colors of the new *Salvia*.

DETAILED BOTANICAL DESCRIPTION

The following is a detailed description of the new cultivar of 7 months in age as grown outdoors in two-gallon containers in Loxely, Ala. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Early commence of bloom and blooms for 28 weeks in Mar del Plata, Argentina.

*Plant type*.—Herbaceous perennial.

*Plant habit*.—Upright and spreading.

*Plant size*.—Reaches about 43 cm in height and 56 cm in spread as grown in a 2-gallon container and up to 1.2 m in height and 60 cm in spread in the landscape.

*Cold hardiness*.—U.S.D.A. Zone 9.

*Diseases and pests*.—No susceptibility or resistance to diseases or pests has been observed.

*Root description*.—Fibrous, non-spreading, 161A in color.

*Propagation*.—Vegetative stem cuttings.

*Growth rate*.—Moderately vigorous.

*Root development*.—20 days for root initiation, 60 days to produce a young plant from rooted cutting.

Stem description:

*Shape*.—4-angled.

*Stem color*.—New growth; N144A suffused with 166A, mature stems; 144B with striations of 166A becoming bark-like at base 144A with striations of 199A.

*Stem size*.—Stem base; about 6 cm in diameter, main stems; an average of 5 mm in diameter and 35 cm in length, lateral branches; average of 4 mm in diameter and up to 19 cm in length.

*Stem surface*.—New growth; pubescent, mature stems; sparsely covered with glandular hairs, base of stem; fissured (bark-like).

*Internode length*.—Average of 4 cm.

*Branching*.—Average of 3 main stems, an average of 5 lateral braches per main stem, an average of 2 sub-lateral flowering branches per lateral branch.

Foliage description:

*Leaf shape*.—Ovate.

*Leaf division*.—Simple.

*Leaf base*.—Cordate.

*Leaf apex*.—Acuminate to acute.

*Leaf fragrance*.—None.

*Leaf venation*.—Pinnate, 144B in color on upper surface, 144D in color on lower surface.

*Leaf margins*.—Serrated.

*Leaf arrangement*.—Opposite.

*Leaf attachment*.—Petiolate.

*Leaf surface*.—Dull, rough to the touch, and densely covered with tiny stiff pubescence on upper and lower surface.

*Leaf size*.—Up to 11 cm in length and 7 cm in width.

*Leaf color*.—Newly expanded leaves; upper surface NN137A and N144A near base, lower surface 137A, mature leaves; upper surface NN137A, lower surface 146A, some leaves have a flush of 79A on the margins.

*Petioles*.—Up to 3 cm in length and 2 mm in width, 145A in color, densely puberulent surface.

Inflorescence description:

*Inflorescence type*.—Terminal branched raceme.

*Lastingness of inflorescence*.—Individual flowers about 5 days on a plant in a container or in the garden, not persistent.

*Inflorescence size*.—An average of 8 cm in length and 7 cm in width.

*Flower type*.—Tubular-bilabiate.

*Flower number*.—An average of 10 flowers and 22 buds per inflorescence at one time.

*Flower fragrance*.—Very faint pleasant fragrance.

*Flower buds*.—Tubular in shape, about 1 cm in length and 6 mm in diameter, a blend of 149A and 144A in color, apex 92A.

*Flower size*.—Average of 4 cm in length and about 1 cm in diameter.

*Peduncle* (*rachis*).—An average of 11 cm in length and 3 mm in width, color N144A and suffused with 166A, surface is densely covered with glandular hairs, flower internode length an average of 4 mm.

*Pedicels*.—About 4 mm in length and 1 mm in width, 183A with a flush of 185B in the middle and 145B at the base in color, surface is pubescent.

*Calyx*.—Tubular, about 6 mm in length and 3 mm in width, persistent for about a week after petals drop.

*Sepals*.—2, fused at base with very apex free that is triangular in shape, 4 mm in length and width, apex mucronate, entire margin, a blend of 149A and 144A in color, in color, surface is finely puberulent and lustrous.

*Petals*.—2, arranged in 2 lips fused into tube at base, tube; about 1.5 cm in length and 7 mm in diameter, 61A with a slight flush of 72A in color, lustrous surface, densely covered with pubescence on outer surface, velvety on inner surface, throat an average of 6 mm in diameter, upper lip; 2-lobed, held upright to tube, curved into renal shape around pistil and stamens, about 1.5 cm in length and 5 mm in width, a blend of 72A, 73A and 72B in color, apex single notched, lower lip; 4-fused lobes, obtuse in shape with sides re-curved, margins entire to slightly wavy in middle section, apex in center 2-notched, base fused, velvety and lustrous on outer and inner surface, each lobe an average of 5 mm in length, as a whole 5 mm in width, inner and outer surface 61A in color.

Reproductive organs:

*Gynoecium*.—Pistil; average of 3 cm in length, 5 mm exerted beyond corolla, style; 2.5 cm in length, 0.8 mm in width and 69C in color with very apex 72B with hairs 72B in color, stigma; bifid with arms about 3 mm in length, linear and pointed in shape and N79A in color, ovary; superior, oblong in shape, about 3 mm in length and 2 mm in diameter and 145C in color.

*Androecium*.—Stamens; 2, filaments; colors are a blend of 71B at top, N75B in middle, and 69D at base, average of 2 cm in length and 1 mm in width, attached to lobe sides with linear arms about 1 mm in length and 69D in color with base flushed 70A in color, fused at base, anthers; average of 5 mm in length, N83A in color and dorsifixed, pollen is abundant in quantity and 18B in color.

*Fruit and seed*.—Observed to be sterile with no viable seeds formed.

It is claimed:

1. A new and distinct cultivar of *Salvia* plant named 'Amante' as herein illustrated and described.

* * * * *